United States Patent [19]

Penman et al.

[11] Patent Number: 4,882,268

[45] Date of Patent: Nov. 21, 1989

[54] METHOD FOR DETERMINING TISSUE OF ORIGIN AND DEGREE OF MALIGNANCY OF TUMOR CELLS

[75] Inventors: Sheldon Penman, Brookline; Edward G. Fey, Boston, both of Mass.

[73] Assignee: Massachusetts Institute of Technology, Cambridge, Mass.

[21] Appl. No.: 812,955

[22] Filed: Dec. 24, 1985

[51] Int. Cl.⁴ .................... C12Q 1/68; C12Q 1/02; G01N 33/53; C07G 15/00

[52] U.S. Cl. .......................................... 435/5; 435/7; 435/29; 435/264; 435/268; 435/269; 435/270; 435/272; 435/6; 436/63; 436/64; 436/548; 530/350; 530/358; 530/387; 530/412; 530/420; 935/78; 536/27

[58] Field of Search ............... 435/948, 6, 7, 5, 29, 435/803, 172.1, 91, 262, 264, 267, 268, 269, 270, 272; 436/63, 64, 548; 530/350, 358, 387, 412, 420; 935/78; 536/27

[56] References Cited

U.S. PATENT DOCUMENTS 4,358,535  11/1982  Falkow ................................. 435/5
4,569,916   2/1986  Penman ............................... 436/64

OTHER PUBLICATIONS

Burdon et al., Biochem. Biophys. Acta., 825(1), 70–79, (May 1985).
Buttyan et al., J. Biol. Chem., 258 (23), 14366–14370 (1983).
Hentzen et al., Proc. Natl. Acad. Sci. U.S.A., 81(2), 304–307, (Jan. 1984).
Hodge et al., J. Cell Biol., 72(1), 194–208 (Jan. 1977).
Intres et al., In Vitro Cell Dev. Biol., 21(11), 641–648 (1985).
*Lehner et al., Exp. Cell Res., 162(1), 205–219 (Jan. 1986).
Mullenders et al., Biochim. Biophys. Acta., 698, 70–77 (1982).
*Moy et al., Cancer Res., 46, 4672–4676 (1986).
Van Eekelen et al., Exp. Cell Res., 141, 181–190 (1982).
Van Eekelen et al., J. Cell Biol., 88, 554–563 (1981).

Van der Velden et al., Biochim. Biophys. Acta., 782(4), 429–436 (1984).
Barrack et al., Recent Progress in Hormone Research, edited by Roy O. Greep, vol. 38, 133–137, and 180–189 (Academic Press, New York, 1982).
Barrack et al., J. Biol. Chem., 255, 7265 (1980).
Berezney et al., Science, 189(4199), 291–293 (Jul. 1975).
Bhorjee et al., J. Cell Biol., 97, 389–396 (1983).
Bodnar et al., Mol. Cell Biol., 3, 1567–1579 (1983).
Briggs et al., J. Cellular Biochem., 21, 249–262 (1983).
*Chaly et al., Cell Biol. Inter. Reports, 10(6), 421–428 (1986).
Chaly et al., Can. J. Biochem. Cell Biol., 63, 644–653 (1985).
Chaly et al., J. Cell Biol., 99, 661–671 (1984).
*Chiu et al., Rad. Res., 107, 24–38 (1986).

(List continued on next page.)

Primary Examiner—Esther M. Kepplinger
Assistant Examiner—Toni R. Scheiner
Attorney, Agent, or Firm—Kilpatrick & Cody

[57] ABSTRACT

A biochemical procedure for diagnosis of three important properties of cells in a biopsy or blood sample: tumor type i.e., the tissue type that has become neoplastic; tissue of origin if the tumor has arisen from a metastasis; and degree of malignancy. The procedure can also be used to obtain antibodies which can be used to determine tissue of origin by immunostaining and to detect tumor antigens appearing in blood by radioimmunoassay.

The procedure consists of isolating and analyzing components of a specific subcellular fraction referred to here as the "nuclear matrix". The nuclear matrix consists of proteins specific to different cell types and nuclear matrix associated DNA. The electrophoretic pattern of the proteins and restriction endonuclease digested DNA is unique and reproducible within a particular cell type and is therefore useful in diagnosing cell type. Changes in these patterns following transformation to a malignant phenotype provide additional diagnostic information.

29 Claims, 5 Drawing Sheets

OTHER PUBLICATIONS

Coffey et al., *Adv. Enzyme Regul.,* 17, 213–248 (1978).
Coffey et al., *Adv. Enzyme Regul.,* 14, 63–100 (1976).
Detke et al., *J. Biol. Chem.,* 257, 3905–3911 (1982).
Eastment et al., *Blood,* 57(4), 747–757 (1981).
Eisenman et al., *Mol. Cell Biol.,* 5(1), 114–126 (1985).
Long et al., *Cell,* 18, 1079–1090 (1979).
Long et al., *Biol. Cell,* 48, 99–108 (1983).
*MacDonald et al., *Biochem. Biophys. Res. Comm.,* 138(1), 254–260 (1986).
Peters et al., *J. Cell Biol.,* 86, 135–155 (1980).
Peters et al., *Eur. J. Biochem.,* 129, 221–232 (1982).
Simmen et al., *Endocrinology,* 115(3), 1197–1202 (1984).
Schmidt et al., *Cancer Res.,* 44, 5291–5304 (1984).
Staufenbiel et al., *Eur. J. Cell Biol.,* 31(2), 341–348 (1983).
Staufenbiel et al., *J. Cell Biol.,* 98, 1886–1894 (1984).
Todorova et al., *Biochem. Biophys. Acta,* 783(1), 36–41 (Oct. 1984).
Werner et al., *Exp. Cell Res.,* 151, 384–395 (1984).
Wojtkowiak et al., *Cancer Res.,* 42, 4546–4552 (1982).
Berezney et al., *J. Cell Biol.,* 73, 616–637 (1977).
Berezney, R., *J. Cell Biol.,* 85, 641–650 (1980).
Comings et al., *Exp. Cell Res.,* 103, 341–360 (1976).
Caizergues-Ferrer et al., *Biochem. Biophys. Res. Com.,* 118(2), 444–450 (Jan. 1984).
Fisher et al., *J. Cell Biol.,* 92(3), 674–686 (1982).
*Flickinger, *Cell Biol. Internat. Reports,* 10(6), 415–420 (1986).
Kaufmann et al., *Exp. Cell Res.,* 132, 105–123 (1981).
Kaufmann et al., *Exp. Cell Res.,* 155(2), 477–495 (1984).
*Kirsch et al., *Biochem. Biophys. Res. Comm,* 137(2), 640–648 (1986).
Milavetz et al., *Virology,* 134(2), 406–420 (1984).
*Milavetz et al., *J. Cell. Physiol.,* 127, 358–396 (1986).
Pienta et al., *J. Cell Sci.,* [Suppl.] 1, 123–125 (1984).
Simmen et al., *J. Cell Biol.,* 99(2), 558–593 (1984).
*Bludau et al., *Exper. Cell Res.,* 165, 269–282 (1986).
*O'Farrell et al., *J. Cell Sci.,* 82, 173–186 (1986).
Capco et al., *Cell,* 29(3), 847–858 (1982).
Fey et al., *Proc. Natl. Acad. Sci. U.S.A.,* 81(14), 4409–4413 (1984).
*Fey et al., *J. Cell Biol.,* 102, 1654–1665 (1986).
Reiter et al., *J. Cell Sci.,* 76, 17–33 (1985).
R. M. Franklin, *J. Cell Biochem.,* 24, 1–14 (1984).
Chem. Abstracts, 99(23), No. 192945A, W. J. Hapbets, *Clin. Exp. Immunol.,* 54(1), 265–276 (1983).
Chem. Abstracts, 101(3), Jul. 1984, No. 19258R, Zbarskii, *Macromol. Funct. Cell,* 1, 114–123 (1980).
Martelli et al., *J. Cell Biol.,* 103,5, part 2, 181 (1986).
*Smith et al., *Mol. Cell. Biochem.,* 70, 151–168 (1986).
Song et al., *J. Biol. Chem.,* 258(5), 3309–3318 (1983).
*Verheijen et al., *J. Cell Sci.,* 80, 103–122 (1986).
*Verheijen et al., *J. Cell Biol.,* 103,5, part 2, 179 (1986).
Wu, B. C. et al., Cancer Research 41, 336–342, (Jan. 1981).
Shelton, K. R. et al., J. Biol. Chem., v.255, No. 22, pp. 10978–10983 (Nov. 1980).
Stastny, J. et al., Clin. Chem., 30/12, 1914–1918 (1984).
Anderson, L. et al., Clin. Chem., 30/12, 1898–1905 (1984).

COLON

METHOD FOR DETERMINING TISSUE OF ORIGIN AND DEGREE OF MALIGNANCY OF TUMOR CELLS

BACKGROUND OF THE INVENTION

The U.S. Government has certain rights in this invention by virtue of National Institute of Health Grant Numbers 5R01 CA08416-20 and 1R01 CA37330-01 and National Science Foundation Grant Number PCM 8309334.

Heretofore, determining the properties of tumor cells has been the province of the clinical pathologist. Diagnosis is based on the morphology of tumor cells in histological preparations. Such diagnosis has serious limitations and cannot always distinguish tumor type and tissue of origin. There is a great need for alternative means of identifying cell type and state of malignancy.

Attempts have been made to determine cell type by analysis of the protein composition of whole cell extracts. However, these extracts contain a number of different proteins, of which the vast majority do not vary between cell types. Even with techniques providing increased resolution between proteins, such as the more recent methods of two dimensional gel electrophoresis, such efforts have largely failed to find differences in protein patterns that could reliably serve as a basis for cell identification.

A significant number of proteins do vary with cell type and can serve as identifying markers. Unfortunately, they are usually present in such small concentration that they are masked in whole cell extracts. There has been limited success in biochemically identifying cells by analyzing the protein composition of a subcellular fraction consisting of the intermediate filaments. The intermediate filaments are proteins present in all cells and can be used to discriminate between five major classes of cells: epithelial, neuronal, glial, muscle and mesenchymal cells such as fibroblasts. Labeled antibodies to these proteins only serve to distinguish among these broad cell classes, although some further discrimination is possible with epithelial cells. In epithelial cells, the intermediate filaments, the keratins, are complex and differ between many types of epithelia. However, the keratins can only be distinguished chemically: antibodies have so far proven unable to discriminate among the keratins. There are also reports that the keratins are altered in some malignancies making their use for fine discrimination uncertain.

All mammalian cells have a nucleus surrounded by the cell cytoplasm. The nucleus contains the cellular DNA complexed with protein and termed chromatin. The chromatin, with its associated proteins, constitutes the major portion of the nuclear mass. The chromatin is organized by the internal skeleton of the nucleus, referred to here as the nuclear matrix.

Although reports describing a nuclear matrix have been published, relatively little is known of its biochemistry and morphology. Although the existence and composition of the matrix is controversial, it is known that the nuclear matrix contains cell-type specific proteins and a small percentage of the total DNA. Current electron microscopy techniques do not image the matrix and reliable methods of separating specific non-chromatin matrix proteins from the much larger quantity of chromatin proteins have not been available.

It is therefore an object of the present invention to provide a method for analyzing the tissue of origin and state of malignancy of tumor cells.

It is a further object of the invention to provide a method which can be performed relatively easily and quickly.

It is a still further object of the invention to provide a method for analyzing tissue of origin which is highly reproducible, objective and can be standardized.

It is another object of the present invention to provide a biochemical method for isolation and analysis of type-specific nuclear matrix proteins and nuclear matrix associated DNA for use in determining malignancy and tissue of origin with much greater resolution than previous methods based on cell specific intermediate filaments.

SUMMARY OF THE INVENTION

A procedure for analyzing tissue of origin and state of malignancy of normal or tumor cells with far greater discrimination than previous methods of identification. The "nuclear matrix", a specific fraction of cell protein constituting only two to four percent of the total protein and six percent of the total DNA of the cell, contains many proteins that differ with cell type and is highly enriched with cell type-specific antigens including highly cell type- and transformation-specific proteins that could not be detected using prior art procedures.

In one embodiment of the method of the present invention, the cell nucleus is isolated, the cytoskeleton proteins and chromatin removed, the nuclear matrix isolated, and the "interior" and "exterior" components of the nuclear matrix separated. The method makes use of the unique properties of the nuclear matrix to achieve complete separation from all other cell constituents. The method is simple, rapid, reproducible, achieves a high degree of matrix purity, is applicable to essentially all types of cells, does not disrupt matrix morphology, and yields most of the biochemically significant matrix components. The method for isolating the nuclear matrix proteins is summarized as follows:

1. Isolation and separation of cells.
2. Separation of soluble cell proteins from the nucleus and cytoskeleton by extraction of membrane lipids and soluble proteins with a non-ionic detergent-physiological salt solution.
3. Separation of cytoskeleton proteins from the nucleus by solubilization of the insoluble cell material from step 2 in either 0.25 M ammonium sulfate pH 6.8 or a detergent-sodium deoxycholate solution.
4. Separation of chromatin from the nuclear matrix by digestion of the insoluble material from step 3 with DNAase I and RNAase in a physiological buffer and elution of the DNA-containing nucleosome with a 0.25 M ammonium sulfate solution buffered to pH 6.8.
5. Separation of the "interior" and "exterior" nuclear matrix proteins by dissolution of the insoluble material from step 4 in a buffer containing between 5 and 10 M urea, preferably 8 M urea and aggregation of the exterior proteins by dialysis into physiological buffer.

In a variation of this procedure, the cytoskeleton proteins and chromatin are removed together by digesting the insoluble material from step 2 with DNAase and RNAase, then extracting with 0.25 M ammonium sulfate at pH 6.8.

In another embodiment of the method, the nuclear matrix associated DNA is isolated and analyzed, alone or in conjunction with the nuclear matrix proteins. The method consists of treating the insoluble material from step 2 with DNAase then 0.25 M ammonium sulfate at physiological pH to remove the chromatin then performing a phenol extraction or centrifuging in $CsCl_2$ to remove any remaining protein. In a variation of this method, the insoluble material from step 2 is digested with a restriction enzyme in the appropriate buffer, the chromatin extracted with 0.25 M ammonium sulfate pH 6.8, then any remaining protein removed by phenol extraction or centrifugation in $CsCl_2$.

Because of the degree of matrix purification obtained with the procedure, several previously unknown properties of the nuclear matrix proteins have been discovered which are useful in the clinical diagnosis of tumor cells. The composition of the matrix proteins is different in every cell type and is further changed when the cell is transformed to the neoplastic state. These proteins can serve to:

1. Identify general cell type (e.g., epithelial, neuronal, etc.) by two-dimensional gel electrophoresis. This serves to classify tumor type.
2. Identify specific cell type (e.g., colon epithelium, breast epithelium, etc.). This serves to locate the origins of metastases.
3. Supply pure antigens to generate tissue specific antibodies for use in immunostaining and radioimmunoassays.
4. Determine the nature and degree of malignancy.

Further characterization is achieved by analyzing and comparing the nuclear matrix associated DNA and, in particular, the restriction endonuclease fragments of nuclear matrix associated DNA.

DETAILED DESCRIPTION OF THE INVENTION

Figure 1:
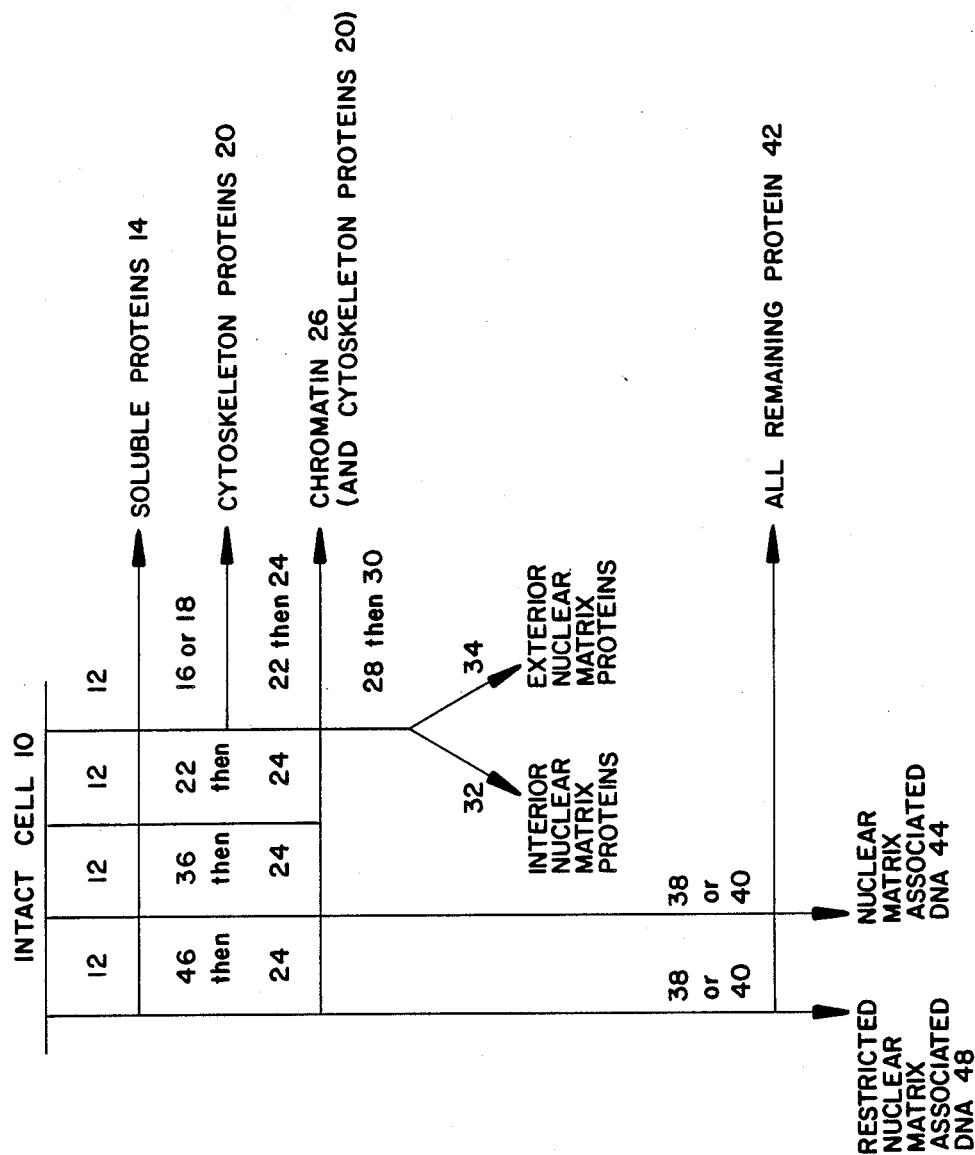
FIG. 1 is a schematic of the isolation and analysis of nuclear matrix proteins and associated DNA according to the present invention.

The present invention is a method for isolating and identifying nuclear matrix proteins and nuclear matrix associated DNA unique to cells of a particular type, some of which are altered by malignancy. The sequential extraction yields subfractions of biochemically distinct cellular proteins and DNA as well as morphologically distinct nuclear matrix structures.

In one embodiment of the invention, the nuclear matrix is purified from a cell suspension prepared from a tissue biopsy or blood sample, separated into its "interior" and "exterior" fractions, and then analyzed by two-dimensional gel electrophoresis. The nuclear matrix proteins account for approximately two to four percent of the total cell protein. The "interior" proteins represent less than one percent of the total protein, with the "exterior" proteins making up the remainder. The designations "interior" and "exterior" are somewhat arbitrary out in general refer to the localization of the proteins within the nucleus. The interior matrix proteins reflect the precise tissue of origin of the cell being examined. The exterior matrix proteins, by virtue of containing the intermediate filaments, reflect the class of the cell being examined (neuronal, epithelial, etc.). Many of the exterior proteins change when cells are transformed to malignancy.

Separating the exterior proteins from the interior matrix proteins has two important results. One, the sensitivity and accuracy with which the interior matrix proteins can be analyzed is greatly enhanced since the exterior matrix proteins amount to greater than one-half of the total protein of the fraction and their presence can obscure some of the minor but important interior matrix proteins. Secondly, the exterior proteins themselves provide two analytic tools. The intermediate filament proteins are useful for quick identification of the class of cell being analyzed and the intermediate filament-associated proteins can serve to quantify the malignant state.

Proteins isolated using the procedure of the present invention are useful as immunogens for the preparation of monoclonal antibodies. The antibodies are conjugated with fluorescent, enzyme or radioactive labels and used as cytological stains on histological sections for detection of tumor antigens in body fluids, and for analysis of proteins separated by two dimensional gel electrophoresis.

The procedures for isolating the interior and exterior nuclear matrix proteins and nuclear matrix associated DNA are as follows:

Cell Preparation

The procedures employ single cells in a suspension. Cells in blood samples or from cell culture are already separate. Tissues obtained by biopsy are dispersed by mild mechanical homogenization followed by digestion with a proteolytic enzyme such as collagenase or trypsin. These enzymes digest connective fibers between cells without affecting the interior contents. In some cases it is desirable to perform an initial, partial separation of cell types. A rapid cell separation is effected by centrifugation, on a Percoll gradient, or other means for rapidly separating cells without chemical interaction.

Purification of the Nuclear Matrix Proteins and Associated DNA

The nuclear matrix is separated from other cell constituents by a series of sequential extractions. The cell suspension is exposed to the extraction solution for one to two minutes and then the insoluble material separated by centrifugation (approximately one to two minutes at 1000 g), filtration (pore size approximately 5 microns), or other method known to those skilled in the art. The sequential fractionation is shown schematically in FIG. 1. The steps are as follows:

1. Removal of soluble cell proteins.

The soluble proteins 14, amounting to 70% of the cell mass, are removed by extracting the intact cell 10 with a non-ionic detergent solution 12, such as 0.5% Triton X-100. The non-ionic detergent in a buffer at physiological pH and ionic strength extracts first the membrane lipids and then the soluble proteins. The detergent solubilizes lipids without denaturing proteins and thus avoids disturbing the integrity of the cell structures. The physiological salt solution is also essential to maintain the morphology of the cytostructure and to prevent the removal of structural elements. An example of a useful buffer is 100 mM NaCl 300 mM sucrose 10 mM PIPES pH 6.8 3 mM $MgCl_2$ 0.5% Triton X-100 1.2 phenylmethylsufonylfluoride at 0° C.

Two dimensional gel analysis of the soluble fraction 10 reveals a complex, dense pattern of major proteins. While many proteins appear to be unique in this fraction, the density of protein spots on the gel precludes more precise analysis.

The remaining skeletal framework, usually masked in conventional Epon-embedded thin section, can be visualized in three dimensions as an unembedded whole mount using the method of Fey et al, in the *J. Cell Biol.*, 98,1973-1984 (1984). For scanning electron microscopy, cells are grown on glass coverslips and fractionated using the method of the present invention. Cells are fixed at various stages of fractionation in the appropriate buffer containing 2.5% gluteraldehyde at 0° C. for 30 minutes followed by rinsing in 0.1 M sodium cacodylate and then 1% $OsO_4$ in 0.1 M Na cacodylate for 5 minutes at 0° C. The cells, still on coverslips, are dehydrated through an ethanol series, dried through the $CO_2$ critical point and sputter-coated with gold-palladium. The whole mount samples are examined in the lower stage of a scanning electron microscope. Transmission electron microscopy is done on cells grown on gold grids which were previously covered with formvar and coated with carbon. Cells are fixed in 2.5% gluteraldehyde and processed as above.

2. Removal of cytoskeleton proteins.

The cytoskeleton proteins 20, consisting of the dense cytoplasmic filament networks, intercellular junctional complexes and apical microcellular structures, is next separated from the nucleus by selective solubilization of the cytoskeleton proteins, amounting to 20% of cell protein mass, with either a 0.25 M ammonium sulfate solution 16 buffered to pH 6.8, for example, 0.25 M ammonium sulfate 0.3 M sucrose 10 mM PIPES pH 6.8 phenylmethylsulfonyl fluoride 0.5% Triton X-100, or with a 1% Tween-40 0.5% sodium deoxycholate solution 18. The nucleus with all of the intermediate filaments still attached, amounting to about 5% of the total cellular protein, remains.

3. Removal of the chromatin.

The chromatin 26, whose association with the nucleus depends on the integrity of DNA and RNA, is next separated from the nuclear matrix. The nucleus is first digested with DNAase and RNAase in near physiological digestion buffer 22, for example, 50 mM NaCl 0.3 M sucrose 10 mM PIPES pH 6.8 3 mM $MgCl_2$ 0.5% Triton X-100 1.2 mM phenylmethylsulfonyl fluoride with 100 micrograms bovine pancreatic DNAse (EC 3.1.4.5, Worthington Biochemical Corp., Freehold, NJ) and 100 micrograms/ml pancreatic RNAse A (EC 3.1.4.22., Sigma Chemical Co., St. Louis, MO). The enzyme cuts DNA principally between the basic units of chromatin or nucleosomes. At this stage, the DNA remains completely in the nucleus in the form of individual nucleosomes. The DNA-containing nucleosomes are then eluted for approximately 5 minutes at 20° C. using 0.25 M ammonium sulfate buffered to pH 6.8 24.

4. Separation of the Interior and Exterior Proteins of the Matrix

The nuclear matrix consists of 2 to 4% of the cell protein mass.

Immunoblot electrophoresis can be used to identify proteins in the nuclear matrix-intermediate filament scaffold fraction, including vimentin, cytokeratins, desmosomal proteins, and specific nuclear matrix proteins. The procedure for immunoblot electrophoresis is as follows. One-dimensional polyacrylamide gels are run according to the method of Laemmli in *Nature (Lond.)*, 227,680-685 (1970). Equal protein concentrations are loaded to compare individual fractions. The reaction of antibodies to protein bands are visualized on nitrocellulose paper according to the procedure of H. Towbin et al., *Proc. Natl. Acad. Sci. U.S.A.*, 76,4350-4354 (1979). Nitrocellulose strips are incubated for 12 hours in 2% hemoglobin in PBS, rinsed three times in PBS, and incubated for 2 hours at 20° C. with antibody to the protein to be detected at the appropriate concentration. Excess antibody is removed by washing with PBS (four 20 minute washes). The strips are then incubated with goat anti-rabbit (or anti-mouse) IgG conjugated to horseradish peroxidase, washed in PBS (four times for a total of 80 minutes) and then developed in 0.4 mg/ml 4-chloro-1-napthol in 0.01% (vol/vol) $H_2O_2$ using the technique of R. Hawkes et al., in *Anal. Biochem.*, 119,142-147 (1982).

The nuclear matrix is further divided into two distinct parts, termed the interior and exterior. The exterior part consists of the intermediate filaments and intermediate filament associated proteins. Although the filaments are exterior to the matrix, in the cytoplasm, they are physically connected to the nuclear surface and behave physiologically as part of the nuclear matrix. They and their associated proteins amount to greater than one-half of the proteins in the matrix preparation.

The interior and exterior matrix proteins are separated by completely dissolving the matrix proteins in a buffered 5 to 10 M urea solution 28, preferably 8 M or as required to completely dissolve the nuclear matrix proteins, and then dialyzing the proteins back into physiological buffer 30. The interior proteins 32 remain in solution. The intermediate filament proteins and associated proteins reassemble into large insoluble filaments 34.

In a variation of the method for isolating the nuclear matrix proteins described above, the cytoskeleton proteins 20 and chromatin 26 are removed together. The soluble proteins 14 are first removed by extraction with a non-ionic detergent buffered solution 12. The insoluble material is digested with DNAase and RNAase in a buffered solution 22 then the cytoskeleton proteins 20 and chromatin 26 extracted with 0.25 M ammonium sulfate at physiological pH 28.

Protein Analysis

The highly purified matrix proteins are analyzed using conventional two-dimensional acrylamide gel electrophoresis. The proteins are first separated in a pH gradient gel according to electrophoretic mobility or isoelectric point. This gel is then placed on a standard 10% acrylamide slab gel and the proteins separated according to molecular weight. One method of two dimensional gel electrophoresis is taught by P. H. O'Farrell in *J. Biol. Chem.* 250, 4007-4021 (1975) using an ampholyte gradient consisting of 90% pH 5-7 (0.4% ampholyte) and 10% pH 3-10 (1.6% ampholyte). The proteins form a pattern of spots, detected by silver staining or by autoradiography, which is diagnostic of the cell type and state of transformation. Equivalent 35$_S$ cpm can be used to facilitate qualitative comparisons.

The matrix preparation is biochemically and morphologically pure by several biochemical criteria. It retains most matrix specific constituents. Freedom from contamination permits a clear and detailed analysis of the matrix proteins by gel electrophoresis.

The two dimensional gel electropherograms yield pure proteins for generating monoclonal antibodies. Monoclonal antibodies are secreted by hybridoma cell lines produced by established immunization and fusion protocols known to those skilled in the art, such as the method of G. Galfre et al., in *Nature (Lond.)* 266,550–552 (1977).

Figure 2A:
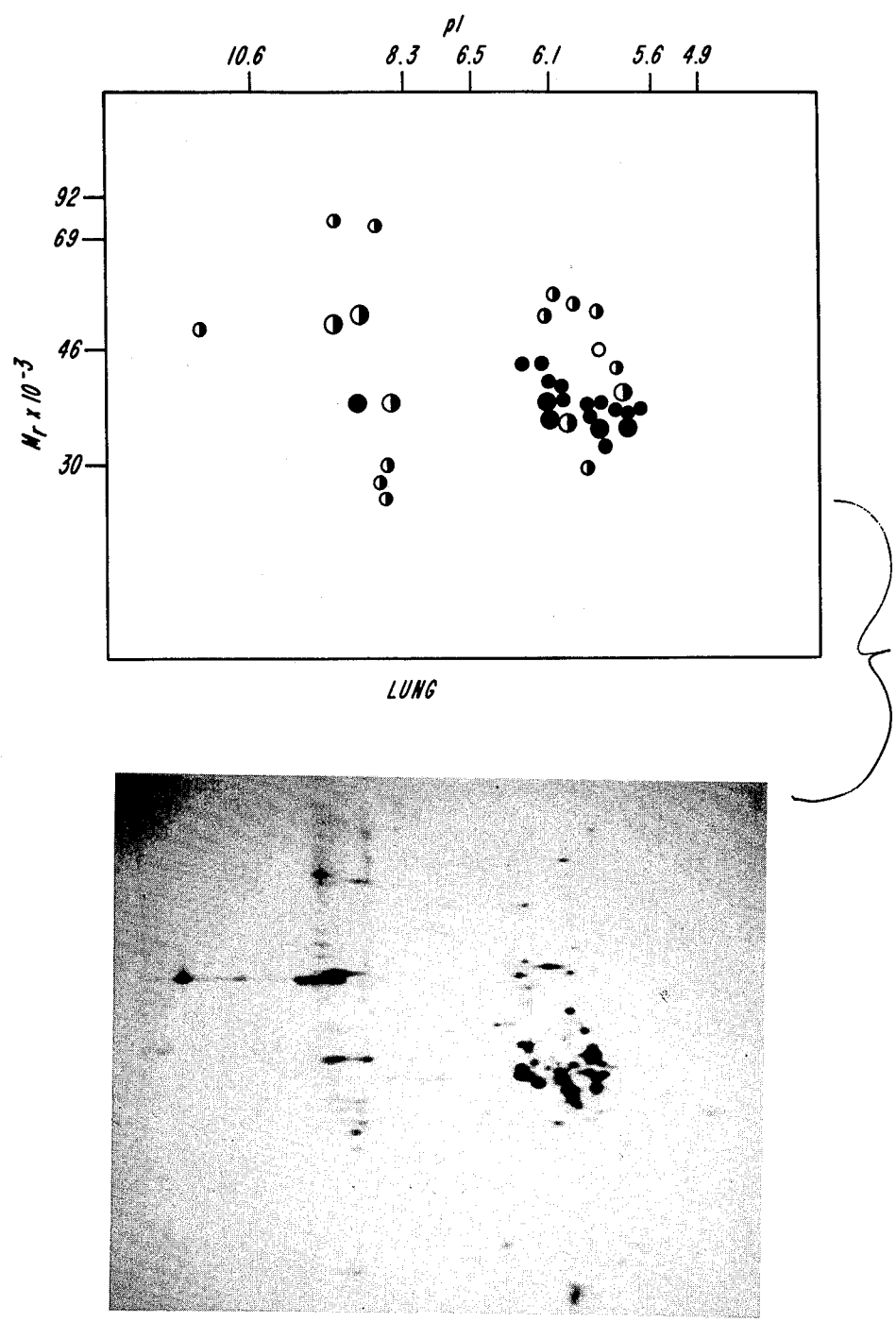
FIGS. 2a and 2a' are a comparison of two dimensional electropherograms (pI vs. m.w.), both actual and diagrammatic, of nuclear matrix proteins from human lung (black circles) and adrenal cortex (white circles) where proteins common to both are shown as half black circles.
Figure 2A:
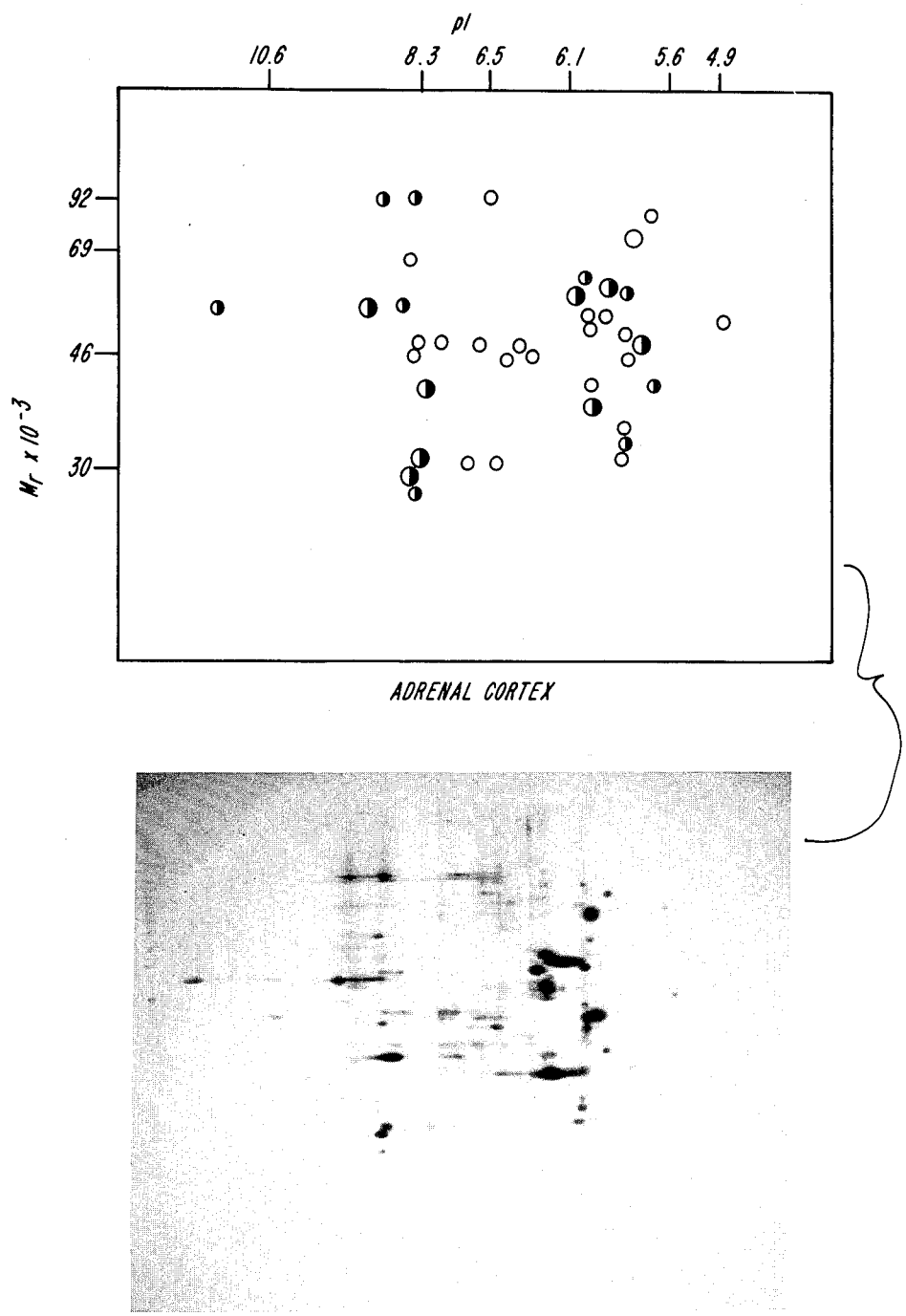
Figure 2B:
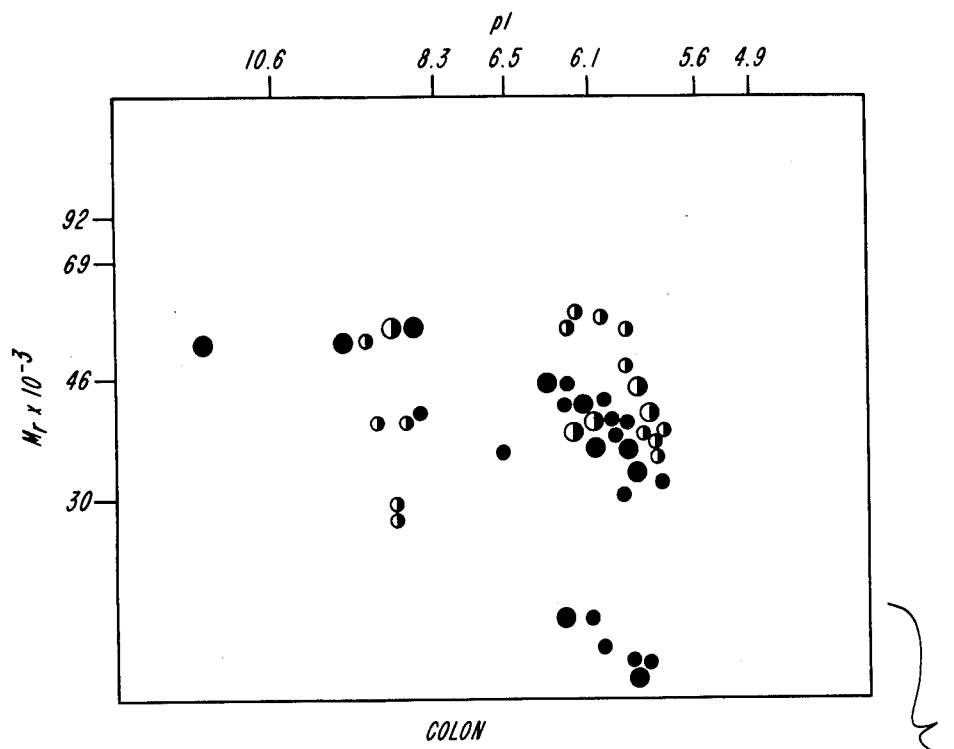
FIGS. 2b and 2b' are a comparison of two dimensional electropherograms (pI vs. m.w.), both actual and diagrammatic, of nuclear matrix proteins from human colon (black circles) and bladder (white circles), where proteins common to both are shown as half black circles.
Figure 2B:
Figure 2B:
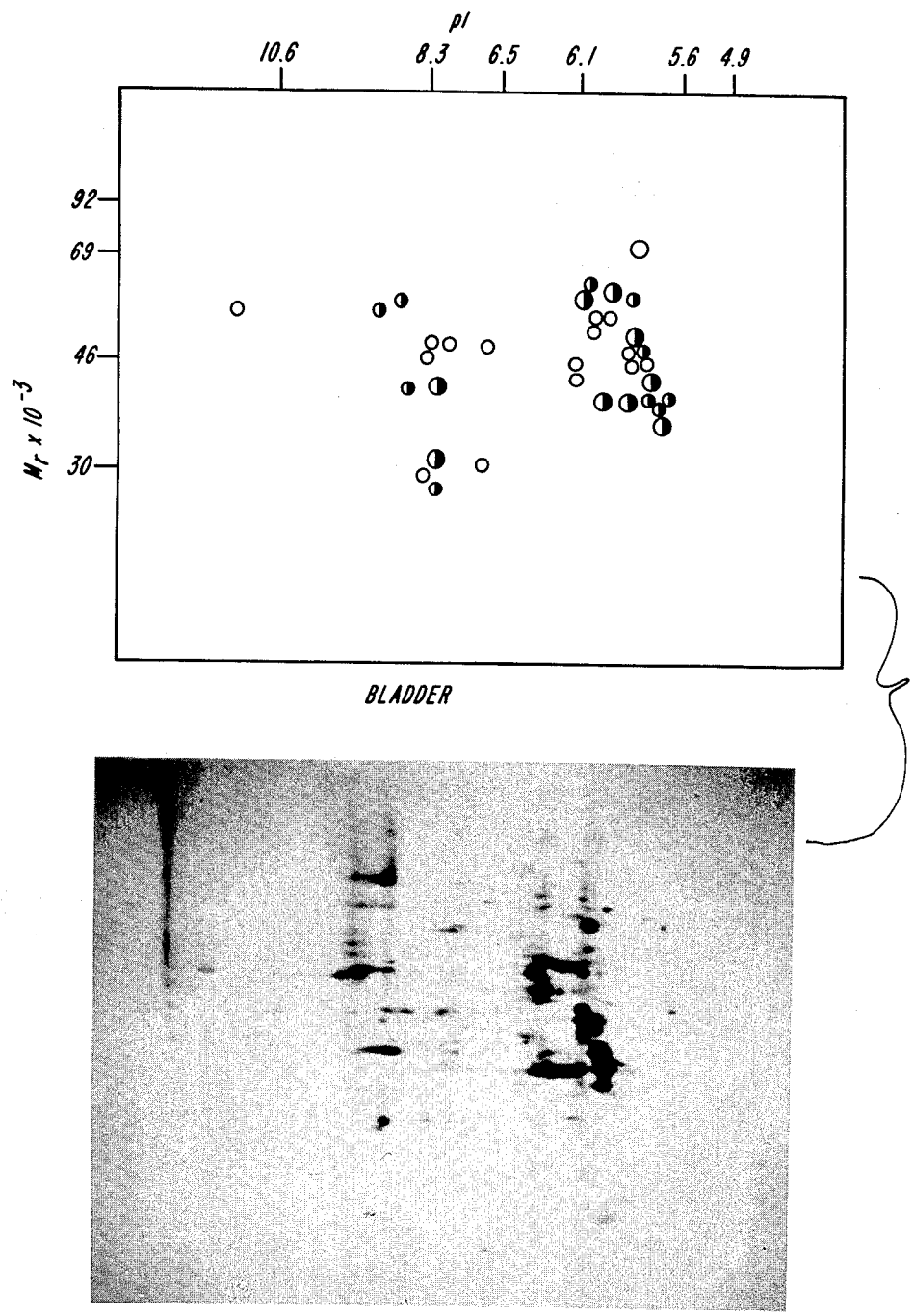

Cell type specificity of matrix proteins has been demonstrated using laboratory cultured cell lines. These include common laboratory lines such as primary and established fibroblasts, HeLa cells, etc. Most relevant to clinical applications are the results from a number of carcinoma lines derived from human biopsy material. As FIGS. 2a, 2a', 2b and 2b', these include human colon, lung, adrenal cortex and bladder cell lines. Although the electropherogram patterns are markedly different in different cell types, each cell type containing unique and common proteins, the patterns for each cell type are completely reproducible. The same results are demonstrable using mouse tissue.

The matrix protein patterns reflect cell transformation. This has been demonstrated in spontaneous transformation of rodent primary fibroblasts, viral transformation of established rodent fibroblasts, transformation of a kidney cell line by transfection with the ras oncogene, and transformation of a kidney cell line by the ultimate carcinogen, BAP diole epoxide using a number of cloned cell lines in each case. Each showed different and marked variation in their matrix protein pattern.

The type and degree of transformation are also closely correlated with changes in matrix protein composition. Of particular interest are the qualitative differences between transformation by the complete carcinogen and by ras gene transfection. Six cloned isolates of cells transformed by ras transfection and 10 isolates of the carcinogen-transformed cells were analyzed. A brief summary of the results is:

a. Transformation by chemical carcinogen leads to the acquisition by the matrix of 12 to 15 new or previously undetected proteins.

b. Transfection by ras results in the loss of about 6 proteins and, in some cases, the acquisition of 2 or 3 new proteins. There appears to be a correlation between the degree of morphological aberrance and the number of matrix protein changes.

The data from transformed cells shows there are different types of transformation events with characteristic signatures.

Analysis of the nuclear matrix associated DNA provides further information for determining the cell type, tissue of origin, and degree of malignancy of cells. All of the "active" DNA in a cell is associated with the nuclear matrix proteins. This DNA represents approximately 6% of the total cell DNA. Approximately one-third (2% of total DNA) is directly bound to the protein portion of the matrix and approximately two-thirds (4% of total DNA) is bound to the RNA component of the nuclear matrix. Different quantities of DNA as well as specific sequences of DNA will be associated with the nuclear matrix and nuclear matrix proteins, depending on cell type and whether the cell is malignant and to what degree. The isolated DNA can be analyzed and identified using gel electrophoresis and blot hybridization with probes specific for a particular unique sequence or repetitive sequence. Probes may be made by inserting the sequence of interest, either a synthetic sequence or a portion of the gene of interest, into a recombinant plasmid using methods known to those skilled in the art.

As shown in FIG. 1, nuclear matrix associated DNA 44 is isolated from the intact cell 10 by extraction of the soluble proteins 14 with a non-ionic detergent in a physiological buffered solution 12, solubilization of the chromatin 26 and cytoskeleton proteins 20 by digestion with DNAase in a physiological buffer 36 followed by extraction into 0.25 M ammonium sulfate at physiological pH 24, and removal of any remaining protein 42 by phenol extraction 38, centrifugation in a cesium chloride gradient 40 or other method known to those skilled in the art. Digestion of the insoluble material with DNAase 36 instead of DNAase in combination with RNAase 22 results in the removal of approximately 94% of the cell DNA instead of approximately 98%.

In another embodiment of this procedure, also shown in FIG. 1, fragments of nuclear matrix associated DNA 48 are prepared by digestion of the insoluble cell material remaining after extraction of the soluble proteins 14 with one or more restriction endonucleases in the appropriate buffer 46, followed by extraction of the cytoskeleton proteins 20 and chromatin 26 in 0.25 M ammonium sulfate at physiological pH 24 and removal of any remaining protein 42 by phenol extraction 38, cesium chloride centrifugation 40, or other method known to those skilled in the art.

Assembling and using the matrix protein and DNA composition data clinically requires construction of a suitable data base. The protein patterns are so different that the initial observations can be by simple visual examination. Additional data can be acquired from cell lines and biopsy and autopsy material. Simple computer aided methods are useful for storing gel pattern information. Comparatively little data processing is necessary since the gel electrophoresis techniques are extremely reproducible and the changes with cell type quite large. Gel patterns are digitized in a simple scanner and stored as a two-dimensional matrix. Stored patterns are displayed in contrasting colors and compared visually. Elaborate pattern analysis programs are not necessary.

One or a few matrix proteins are usually sufficient for diagnosis of tissue type. The high degree of purity of these proteins allows them to serve as antigens for tissue specific monoclonal antibodies. Antibodies are used singly or in a panel to analyze the tissue of origin or presence of tumor derived or altered proteins. Spots are cut from a preparative two-dimensional gel and used for immunization. The colonies are screened using an assay such as an enzyme (ELIZA) or radioimmunoassay (RIA) based on matrices from the target cell type. The availability of highly specific antibodies permits use as RIA reagents. Tumor cells may be detectable in some cases by circulating antigens from necrotic cells.

The extremely rapid, simple, extraction and analytical procedure of the present invention provides a means for an objective determination of the tissue of origin of tumor cells, thereby indicating whether transformation of normal cells has occurred and to what degree and whether there has been metastasis. The isolation of the nuclear matrix proteins and loading onto standardized, commercially available two-dimensional gels takes less than thirty minutes. The time to run the gel varies according to the desired degree of resolution, the amount of protein applied to the gel, and other variables familiar to those skilled in the art. As previously noted, a computer with an extensive data bank can be used for rapid, reproducible analysis of the gel pattern. Conceivably, the system could be automated for use within the time frame of a surgical procedure.

Although this invention has been described with reference to specific embodiments, variations and modifications of the method for isolating and diagnosing nuclear matrix proteins and associated DNA from cells of unknown tissue type or state of malignancy will be obvious to those skilled in the art. It is intended that such modifications and variations fall within the scope of the appended claims.

What is claimed is:

1. A method for determining the tissue of origin of a cell and degree the presence of malignancy comprising:
   (a) isolating interior nuclear matrix proteins from at least one type of cell of known origin;
   (b) separating the isolated nuclear matrix proteins by two-dimensional gel electrophoresis and detecting proteins specific to the type of cells;
   (c) isolating interior nuclear matrix proteins from cells of unknown origin;
   (d) separating the nuclear matrix proteins from cells of unknown origin by two-dimensional gel electrophoresis;
   (e) comparing the separated interior nuclear matrix proteins from cells of unknown origin with the separated, identified interior nuclear matrix proteins of known origin; and
   (f) determining the tissue of origin and the presence of malignancy of the cell of unknown origin.

2. The method of claim 1 wherein the interior nuclear matrix proteins are isolated from proteins soluble in a physiological detergent solution, cytoskeleton proteins, chromatin, and the exterior nuclear matrix proteins including the intermediate filaments by:
   (a) extracting eucaryotic cells with a non-ionic detergent solution at physiological pH and ionic strength to extract the proteins in the nucleus and cytoskeleton which are soluble in the physiological detergent solution;
   (b) separating the nuclear matrix proteins from the cytoskeleton proteins remaining in the extracted cells of step a by solubilizing the cytoskeleton proteins in a solution which does not dissolve the nuclear proteins;
   (c) separating the chromatin from the nuclear matrix proteins by digesting the insoluble material from step b with DNAse and RNAase and dissolving the chromatin with a buffered ammonium sulfate solution;
   (d) separating the interior and exterior proteins of the nuclear matrix by first dissolving the insoluble nuclear matrix proteins from step c in urea and then dialyzing the dissolved proteins back into a physiological buffer, wherein the interior nuclear matrix proteins, are soluble in the physiological buffer and the exterior nuclear matrix proteins are insoluble.

3. The method of claim 2 wherein the cytoskeleton proteins are solubilized in 0.25 M ammonium sulfate at pH 6.8.

4. The method of claim 2 wherein the cytoskeleton proteins are solubilized in a solution comprising a non-ionic detergent and sodium deoxycholate.

5. The method of claim 2 wherein the cytoskeleton proteins and chromatin are removed together by digesting the insoluble material from step a with DNAase and RNAase and then eluting with 0.25 M ammonium sulfate at pH 6.8.

6. The method of claim 1 wherein the separated nuclear matrix proteins of step d are visualized by staining the gel to form a pattern of the separated proteins.

7. The method of claim 1 further comprising making antibodies to the isolated, separated interior nuclear matrix proteins of step d from either the cells of known or unknown origin.

8. The method of claim 7 further comprising labeling the interior nuclear matrix protein antibodies, wherein the isolated interior nuclear matrix proteins of unknown cell origin are detected by reacting said proteins from cells of unknown origin with labeled antibodies to nuclear matrix proteins of known origin.

9. The method of claim 1 further comprising compiling a data base consisting of two-dimensional gel electrophoresis patterns of isolated interior nuclear matrix proteins from cells of different malignancy and tissue of origin.

10. The method of claim 1 further comprising isolating the exterior nuclear matrix proteins from cells of known and unknown origin and comparing the exterior nuclear matrix proteins from cells of unknown origin with exterior nuclear matrix proteins from cells of known origin.

11. A method for detecting tumor antigens associated with cells containing specific interior nuclear matrix proteins in a body fluid comprising
   (a) reacting at least one labeled monoclonal antibody to an interior nuclear matrix protein from cells of known origin and degree of malignancy with the body fluid to be analyzed; and
   (b) detecting the presence of protein recognized by said antibody to interior nuclear matrix protein from cells of known origin and degree of malignancy in the body fluid.

12. The method of claim 11 further comprising:
isolating interior nuclear matrix protein associated DNA from at least one cell of known origin;
isolating interior nuclear matrix protein associated DNA from cells of unknown origin; and
comparing the isolated nuclear matrix associated DNA from the cells of known and unknown origin.

13. The method of claim 12 further comprising digesting the nuclear matrix associated DNA with restriction enzymes before comparing the DNA from cells of known and unknown origin.

14. The method of claim 12 wherein the nuclear matrix associated DNA is isolated by:
   (a) separating the soluble proteins from the nucleus and cytoskeleton by extracting eucaryotic cells with a non-ionic detergent solution at physiological pH and ionic strength;
   (b) digesting the insoluble material from step a with DNAase and then eluting with a buffered ammonium sulfate solution; and
   (c) removing any remaining protein from the insoluble material in step b.

15. The method of claim 13 wherein the nuclear matrix associated DNA is isolated by:

(a) separating the soluble proteins from the proteins and nucleic acid insoluble in a non-ionic detergent solution at physiological pH and ionic strength in the nucleus and cytoskeleton by extracting eucaryotic cells with a non-ionic detergent solution at physiological pH and ionic strength;

(b) digesting the insoluble protein and nucleic acid from step a with one or more restriction enzymes in the appropriate buffer and then eluting with a buffered ammonium sulfate solution; and (c) removing any remaining protein from the insoluble protein and nucleic acid from step b.

16. The method of claim 12 wherein the nuclear matrix associated DNA is isolated by:

(a) separating the soluble proteins from the proteins and nucleic acid insoluble in a non-ionic detergent solution at physiological pH and ionic strength in the nucleus and cytoskeleton by extracting eucaryotic cells with a non-ionic detergent solution at physiological pH and ionic strength;

(b) digesting the insoluble protein and nucleic acid from step a with DNAase and then eluting with a buffered ammonium sulfate solution; and (c) removing any remaining protein from the insoluble DNAase digested protein and nucleic acid in step b.

17. The method of claim 16 wherein the cytoskeleton proteins are solubilized in 0.25 M ammonium sulfate at pH 6.8.

18. The method of claim 16 wherein the cytoskeleton proteins are solubilized in a solution comprising a non-ionic detergent and sodium deoxycholate.

19. The method of claim 16 wherein the insoluble material of step C is dissolved in a buffered solution comprising 8 M urea.

20. Antibodies to interior nuclear matrix proteins isolated according to the method of claim 16.

21. A method for isolating nuclear matrix associated DNA comprising:

(a) extracting eucaryotic cells with a non-ionic detergent solution at physiological pH and ionic strength to extract the proteins in the nucleus and cytoskeleton which are soluble in the physiological detergent solution;

(b) separating the nuclear matrix proteins from the cytoskeleton proteins remaining in the extracted cells of step a by solubilizing the cytoskeleton proteins in a solution which does not dissolve the nuclear proteins;

(c) separating the chromatin from the nuclear matrix by digesting the insoluble nuclear proteins and nucleic acid from step b with DNAse and RNAase and then dissolving the digested insoluble material with a buffered ammonium sulfate solution; and (d) removing any remaining protein from the insoluble nuclear proteins and nucleic acid from step c using a method which extracts protein and not nucleic acid.

22. The method of claim 21 wherein in step d the remaining protein is removed by phenol extraction.

23. The method of claim 21 wherein in step d the remaining protein is removed by centrifugation in cesium chloride.

24. The method of claim 21 wherein the digested material in step b is eluted with 0.25 M ammonium sulfate pH 6.8.

25. A method for isolating restriction fragments of nuclear matrix associated DNA comprising:

(a) extracting eucaryotic cells with a non-ionic detergent solution at physiological pH and ionic strength to extract the proteins in the nucleus and cytoskeleton which are soluble in the physiological detergent solution;

(b) digesting the insoluble proteins and nucleic acid from step a with one or more restriction enzymes in the appropriate buffer and then dissolving the digested material into a buffered ammonium sulfate solution; and (c) removing any remaining protein from the dissolved insoluble proteins and nucleic acid in step c using a method which extracts protein and not nucleic acid.

26. The method of claim 25 wherein the cytoskeleton proteins are solubilized in 0.25 M ammonium sulfate at pH 6.8.

27. The method of claim 25 wherein the cytoskeleton proteins are solubilized in a solution comprising a non-ionic detergent and sodium deoxycholate.

28. The method of claim 25 wherein in step c the insoluble protein is dissolved in a buffered solution comprising 8 M urea.

29. The method of claim 1 further comprising selecting the cells of known origin of step a from cells containing nucleotide sequences of viral origin.

* * * * *

UNITED STATES PATENT AND TRADEMARK OFFICE
CERTIFICATE OF CORRECTION

PATENT NO. : 4,882,268

DATED : November 21, 1989

INVENTOR(S) : Sheldon Penman, et al.

Page 1 of 2

It is certified that error appears in the above-identified patent and that said Letters Patent is hereby corrected as shown below:

Column 9, line 20, delete "degree".

Column 10, line 56, cancel beginning with "14. The method of Claim 12" to and including "ble material in step b." in column 11, line 66, and insert the following claim:

--14. The method of Claim 12 wherein the nuclear matrix associated DNA is isolated by:

(a) separating the soluble proteins from the proteins and nucleic acid insoluble in a non-ionic detergent solution at physiological pH and ionic strength in the nucleus and cytoskeleton by extracting eucaryotic cells with a non-ionic detergent solution at physiological pH and ionic strength;

(b) digesting the insoluble protein and nucleic acid from step a with DNAase and then eluting with a buffered ammonium sulfate solution; and (c) removing any remaining protein from the insoluble DNAase digested protein and nucleic acid in step b.--

Column 11, line 13, cancel beginning with "16. The method of Claim 12 wherein" to and including "step b." in column 11, line 26, and insert the following claim:

--16. A method for isolating interior nuclear matrix proteins from eucaryotic cells comprising:

(a) extracting eucaryotic cells with a non-ionic detergent solution at physiological pH and ionic strength to extract the proteins in the nucleus and cytoskeleton which are soluble in the physiological detergent solution;

(b) separating the nuclear matrix proteins from the cytoskeleton proteins remaining in the extracted cells of step a by solubilizing the cytoskeleton proteins in a

UNITED STATES PATENT AND TRADEMARK OFFICE
CERTIFICATE OF CORRECTION

PATENT NO. : 4,882,268

DATED : November 21, 1989

INVENTOR(S) : Sheldon Penman, et al.

It is certified that error appears in the above-identified patent and that said Letters Patent is hereby corrected as shown below:

solution which does not dissolve the nuclear matrix proteins;
    (c) separating the chromatin from the nuclear matrix proteins by digesting the insoluble material from step b with DNAase and RNAase and dissolving the chromatin with a buffered ammonium sulfate solution;
    (d) separating the interior and exterior proteins of the nuclear matrix by first dissolving the insoluble nuclear matrix proteins from step c in urea, then dialyzing the dissolved proteins back into a physiological buffer, wherein the interior nuclear matrix proteins are soluble in the physiological buffer and the exterior nuclear matrix proteins are insoluble, and removing the insoluble exterior matrix proteins from the solution.--

Signed and Sealed this

Twenty-fifth Day of May, 1993

Attest:

MICHAEL K. KIRK

Attesting Officer      Acting Commissioner of Patents and Trademarks